(12) United States Patent
Dubovoy et al.

(10) Patent No.: US 11,179,304 B2
(45) Date of Patent: *Nov. 23, 2021

(54) CLEANSING BARS

(71) Applicant: Colgate-Palmolive Company, New York, NY (US)

(72) Inventors: Viktor Dubovoy, Cresskill, NJ (US); Jeffrey Mastrull, Flemington, NJ (US); Daniel Talancon, Mexico City (MX); David Santos, Edison, NJ (US); Laurence D. Du-Thumm, Princeton, NJ (US); Long Pan, Somerset, NJ (US); Abraham Cazes, Edo Mex (MX); Enrique Valencia Garcia, Delegación Miguel Hidalgo (MX)

(73) Assignee: Colgate-Palmolive Company, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/023,817

(22) Filed: Sep. 17, 2020

(65) Prior Publication Data

US 2021/0000713 A1    Jan. 7, 2021

Related U.S. Application Data

(63) Continuation of application No. 16/066,874, filed as application No. PCT/US2015/068231 on Dec. 31, 2015, now Pat. No. 10,821,059.

(51) Int. Cl.
| | | |
|---|---|---|
| *A61K 8/00* | (2006.01) | |
| *A61K 8/34* | (2006.01) | |
| *A61K 8/49* | (2006.01) | |
| *A61Q 17/00* | (2006.01) | |
| *A61Q 19/10* | (2006.01) | |
| *A61K 8/02* | (2006.01) | |

(52) U.S. Cl.
CPC .............. *A61K 8/34* (2013.01); *A61K 8/0216* (2013.01); *A61K 8/347* (2013.01); *A61K 8/4926* (2013.01); *A61Q 17/005* (2013.01); *A61Q 19/10* (2013.01)

(58) Field of Classification Search
CPC ......... A61K 8/34; A61K 8/347; A61K 8/4926
See application file for complete search history.

(56) References Cited

U.S. PATENT DOCUMENTS

| | | | |
|---|---|---|---|
| 6,457,333 B1 * | 10/2002 | Shelton .................. | D04B 35/04 66/121 |
| 6,825,161 B2 | 11/2004 | Shefer et al. | |
| 8,729,137 B2 | 5/2014 | Ansari et al. | |
| 8,877,234 B2 | 11/2014 | Waltraud et al. | |
| 9,060,952 B2 | 6/2015 | Nunez et al. | |
| 9,750,667 B2 | 9/2017 | Misner et al. | |
| 2007/0196313 A1 | 8/2007 | Scala et al. | |
| 2011/0229417 A1* | 9/2011 | Gurge .................. | A61K 9/0014 424/45 |
| 2013/0059929 A1* | 3/2013 | Koehler ............... | A61K 31/195 514/784 |
| 2013/0156708 A1 | 6/2013 | Pesaro et al. | |
| 2017/0002297 A1* | 1/2017 | Klug .................... | C11D 3/3472 |
| 2019/0008734 A1 | 1/2019 | Dubovoy et al. | |

FOREIGN PATENT DOCUMENTS

| | | |
|---|---|---|
| CN | 1649994 | 8/2005 |
| CN | 101123940 | 2/2008 |
| JP | 2006-045127 | 2/2006 |
| WO | 2009/146800 | 12/2009 |
| WO | 2014/191181 | 12/2014 |
| WO | 2014/191197 | 12/2014 |
| WO | 2017/116457 | 7/2017 |

OTHER PUBLICATIONS

Beiersdorf, 2015, "In-Shower Moisturizer Body Lotion for Dry Skin," Mintel GNPD AN: 3549169.
Hygienic Standard for Cosmetics; p. 72; Ministry of Health of the People's Republic of China; Jan. 31, 2007.
International Search Report and Written Opinion of the International Searching Authority in International Application No. PCT/US2015/068231, dated Mar. 7, 2016.
Kaya, 2015, "Anti-Dandruff Shampoo," Mintel GNPD AN: 3676063.
Klein et al., 2007, "A new generation of preservatives for cosmetic formulations—Nipaguard® PO 5, Nipaguard® POB and Nipaguard® POM," Cosmetic Science Technology, pp. 174-179.
Laboratoires Dermatologiques D'uriage, 2015, "Dermatological Bar," Mintel GNPD AN: 3537331.
Lilleborg, 2015, Intensive Hand Cream, Mintel GNPD AN: 2955589.
Mandom, 2012, "Double Care Anti Dandruff Treatment Hair Cream," Mintel GNPD AN: 1895960.
Manual of Toxicity of Chemicals and Their Environmental Protection Parameters; p. 404; Huamo Dong (chief aditor); Mar. 31, 1988.
Medical Troubleshooting; pp. 298-299; Ministry of Health, General Logistics Department of the Chinese People's Liberation Army; Dec. 31, 1984.

\* cited by examiner

*Primary Examiner* — Necholus Ogden, Jr.

(57) ABSTRACT

Described herein, are personal care compositions comprising a cleanser base comprising at least one cleanser selected from a soap and a surfactant; and an effective amount of an antibacterial system comprising a combination of phenoxyethanol and piroctone, or a salt thereof. Methods of making and using these compositions are also described.

13 Claims, No Drawings

CLEANSING BARS

BACKGROUND

Bar soaps are popular products for body cleansing. Some bar soaps contain one or more compounds that possess antibacterial properties to provide effective cleansing. One such compound which has been used extensively in bar soap formulations is triclocarban, (i.e., 3-(4-chlorophenyl)-1-(3, 4-dichlorophenyl)urea).

However, there is a continuing need for novel and effective antibacterial systems for personal cleansing applications, such as bar soaps. The present invention is directed to this, as well as other, important ends.

BRIEF SUMMARY

It has surprisingly been found that a combination of phenoxyethanol and piroctone, or a salt thereof such as piroctone olamine, can provide excellent antibacterial efficacy in a personal care cleansing composition, and in particular, bar soaps. Thus, in some embodiments, the present disclosure provides a cleansing composition comprising: at least one cleanser chosen from soaps and surfactants; and an antibacterial system; wherein the antibacterial system comprises an effective amount of a combination of phenoxyethanol and piroctone, or a salt thereof. In some embodiments, the cleansing composition is a bar soap or cleansing bar. In some embodiments, the piroctone or a salt thereof is, or includes, piroctone olamine. In some embodiments, the cleansing composition further includes petrolatum (also known as petroleum jelly, soft paraffin or multi-hydrocarbon, CAS number 8009-03-8).

In further embodiments, the present disclosure provides methods for preparing a bar soap cleansing composition, said bar soap cleansing composition comprising phenoxyethanol and piroctone, or a salt thereof, wherein the method comprises the steps of providing a mixture or solution comprising piroctone, or a salt thereof, in a solvent; and incorporating the mixture or solution into a bar soap formulation. In some embodiments, the solvent can be the phenoxyethanol; or propylene glycol; or mixtures of both.

In further embodiments, the present disclosure provides methods for removing bacteria from skin; and methods for inhibiting bacterial growth on skin; comprising washing skin with a cleansing composition as disclosed herein.

DETAILED DESCRIPTION

Unless otherwise specified, all percentages and amounts expressed herein and elsewhere in the specification should be understood to refer to percentages by weight. As used throughout, ranges are used as shorthand for describing each and every value that is within the range. Any value within the range can be selected as the terminus of the range.

As used herein, the term "cleansing bar" or "bar soap" includes, but is not limited to, bars for cleansing and personal hygienic use comprising a cleanser chosen from soap and surfactant. The cleansing bar may be a soap bar (soap is the cleanser), syndet (non-soap surfactant is the cleanser), or combar (a mixture of soap and surfactant).

The present disclosure provides cleansing compositions, and in particular cleansing bars, containing an antibacterial system that includes phenoxyethanol and piroctone, or a salt thereof, which is preferably piroctone olamine.

In one exemplary embodiment, the present disclosure thus provides a cleansing composition (Composition 1) comprising:
at least one cleanser chosen from soaps and surfactants; and
an antibacterial system;
wherein the antibacterial system comprises an effective amount of a combination of phenoxyethanol and piroctone, or a salt thereof; for example any of the following compositions:

1.1 Composition 1, wherein the composition is a cleansing bar;

1.2 Composition 1 or 2, wherein the piroctone or a salt thereof comprises piroctone olamine;

1.3 Any preceding Composition 1 et seq., wherein the antibacterial system comprises an effective amount of a combination of phenoxyethanol and piroctone olamine;

1.4 Any preceding Composition 1 et seq., wherein the phenoxyethanol is present in an amount of from 0.01% to 2% by weight; 0.1% to 1.25% by weight; 0.5% to 1% by weight; 0.65% to 0.85% by weight; or about 0.75% by weight of the cleansing composition; and the piroctone, or salt thereof, is present in an amount of from 0.01% to 1.5% by weight; from 0.01% to 1% by weight; from 0.01% to 0.5% by weight; from 0.05% to 0.3% by weight; from 0.05% to 0.15% by weight; or about 0.1% by weight, or about 0.3% by weight of the cleansing composition;

1.5 Any preceding Composition 1 et seq., wherein the phenoxyethanol is present in an amount of from 0.01% to 2% by weight of the cleansing composition; and the piroctone, or salt thereof, is present in an amount of from 0.01% to 1.5% by weight of the cleansing composition;

1.6 Any preceding Composition 1 et seq., wherein the phenoxyethanol is present in an amount of from 0.1% to 1.25% by weight of the cleansing composition; and the piroctone, or salt thereof, is present in an amount of from 0.05% to 0.3% by weight of the cleansing composition;

1.7 Any preceding Composition 1 et seq., wherein the phenoxyethanol is present in an amount of from 0.5% to 1% by weight of the cleansing composition; and the piroctone, or salt thereof, is present in an amount of from 0.05% to 0.15% by weight of the cleansing composition;

1.8 Any preceding Composition 1 et seq., wherein the phenoxyethanol is present in an amount of from 0.65% to 0.85% by weight of the cleansing composition; and the piroctone, or salt thereof, is present in an amount of from 0.05% to 0.15%, or 0.2% to 0.4% by weight of the cleansing composition;

1.9 Any preceding Composition 1 et seq., wherein the phenoxyethanol is present in an amount of about 0.75% by weight of the cleansing composition; and the piroctone, or salt thereof, is present in an amount about 0.3% by weight of the cleansing composition, or about 0.1% by weight of the composition;

1.10 Any preceding Composition 1 et seq., wherein the cleansing composition further comprises petrolatum;

1.11 Composition 1.10, wherein the petrolatum is present in an amount of from 0.1-05% by weight of the cleansing composition;

1.12 Composition 1.10, wherein the petrolatum is present in an amount of from 0.1-2% by weight of the cleansing composition;

1.13 Composition 1.10, wherein the petrolatum is present in an amount of from 0.1-1% by weight of the cleansing composition;

1.14 Composition 1.10, wherein the petrolatum is present in an amount of from 0.3-0.9% by weight of the cleansing composition;
1.15 Composition 1.10, wherein the petrolatum is present in an amount of from 0.3-0.7% by weight of the cleansing composition;
1.16 Composition 1.10, wherein the petrolatum is present in an amount of from 0.3-0.5% by weight of the cleansing composition;
1.17 Any preceding Composition 1 et seq., wherein the cleansing composition comprises one or more soaps and/or surfactants;
1.18 Composition 1-1.17, wherein the cleansing composition comprises one or more surfactants and/or soaps selected from soap chips; anionic surfactants; nonionic surfactants; cationic surfactants; amphoteric surfactants; and zwitterionic surfactants.
1.19 Any preceding Composition 1 et seq., wherein the cleansing composition comprises one or more additional components selected from binders, foam boosters, coloring agents, dyes, pigments, fragrances, preservatives, fillers, exfoliating/scrubbing particles, pearlizers, inorganic salts, brighteners, sequestering agents, opacifiers, free fatty acids, chelating agents (e.g., EDTA), humectants (e.g., polyols, for example, glycerol), antibacterial agents, polymers, and any combination thereof;
1.20 Any preceding Composition 1 et seq., wherein the at least one cleanser component comprises from about 20, 30, 40, 50 or 60% by weight of the composition to about 70, 80, 85, 90 or 95% by weight of the composition.

The cleansing bar of the present disclosure includes at least one cleanser component. The terms "cleansing agent" and "cleanser" interchangeably refer to soap and/or surfactant. The terms are used to refer to soap alone, surfactant alone, or a combination of soap and surfactant. The amount of cleansing agent in the cleansing bars of the present disclosure can be from 10% to 95% by weight of the composition; for example from about 20, 30, 40, 50 or 60% by weight of the composition to about 70, 80, 85, 90 or 95% by weight of the composition. In certain embodiments, the amount of cleansing agent in the cleansing bars of the present disclosure is 50% to 85%; or from 55% to 80%, or from 60% to 75%, by weight of the composition.

The term "soap" refers to the salts of fatty acids that are typically used to make soap bars. Exemplary soaps can include blends of $C_{16}$-$C_{18}$ and $C_{12}$-$C_{14}$ fatty acids; for example a 65-85 weight % of $C_{16}$-$C_{18}$ and 15-35 weight % of $C_{12}$-$C_{14}$ fatty acids based on the total weight of the soap. The $C_{16}$-$C_{18}$ fatty acids can be obtained from tallow, and the $C_{12}$-$C_{14}$ fatty acids can be obtained from lauric, palm kernel, or coconut oils. Suitable ingredients and amounts are: 65 weight % sodium soap, 15 weight % water, 7 weight % glycerin, 0.7 weight % sodium chloride, 0 weight % sodium hydroxide, and optionally a talc, all together in a glycerin base.

In certain embodiments the cleanser component is or includes a hydrophilic soap chip (e.g., "a base component"). The soap chips useful herein for the purpose of this disclosure also include but are not limited to the well known alkali metal salts of aliphatic (alkanoic or alkenoic) acids having about as 8 to 22 carbon atoms alkyl, preferably 10 to 20 carbon atoms alkyl chain. These may be described as alkali metal carboxylates of acrylic hydrocarbons having about 12 to about 22 carbon atoms. Any other surfactant can also be present in the soap chip such as those mentioned in U.S. Pat. No. 5,139,781 at column 5, line 35 to column 11, line 46. In certain embodiments, the amount of soap is 8 to 20 weight % of the total composition. In some embodiments, sodium soaps are used in the compositions of the present disclosure. In some such embodiments, from 1% to 25% of the soap may be ammonium, potassium, magnesium, calcium soaps or a mixture of these soaps.

Soaps having the fatty acid distribution of common vegetable oils may be suitable, e.g., palm kernel oil, palm oil, coconut oil, olive oil or laurel oil, or the fatty acid distribution of tallow (rendered animal fat). The soap may comprise the fatty acid distribution of any combination of natural or synthetic fatty acid sources (e.g., any combination of natural animal or vegetable fats or oils, and/or individual fatty acids).

Surfactant refers to any anionic, nonionic, cationic, amphoteric, or zwitterionic surfactant. The total amount of surfactant can be any desired amount. In certain embodiments, the amount of surfactant in the cleansing bar is 1 to 25 weight %, or 1 to 15 weight %. Examples of anionic surfactant include, but are not limited to, alkyl($C_6$-$C_{22}$) materials such as alkyl sulfates, alkyl sulfonates, alkyl benzene sulfonates, lauryl sulfates, lauryl ether sulfates, alkyl phosphates, alkyl ether sulfates, alkyl alpha olefin sulfonates, alkyl taurates, alkyl isethionates (SCI), alkyl glyceryl ether sulfonates (AGES), sulfosuccinates and the like. These anionic surfactants can be alkoxylated, for example, ethoxylated, although alkoxylation is not required. These surfactants are typically highly water soluble as their sodium, potassium, alkyl and ammonium or alkanol ammonium containing salt form and can provide high foaming cleansing power. In certain embodiments, examples of anionic surfactants include, but are not limited to, sodium lauryl ether (laureth) sulfate (average of 2 to 15 EO per mole, such as 2, 3, 4, or 5) sodium cocoyl isethionate, and sodium cocoyl methyl isethionate. For laundry, examples of anionic surfactants include, but are not limited to, alkyl sulfates, such as sodium lauryl sulfate, ammonium alkyl sulfate salts, alkyl ethoxylate sulfates, alkylbenzene sulfonates, such as dodecylbenzene sulfonate, nonionic surfactants, polyethoxylated alcohols, such as $C_{12}$-$C_{13}$ alcohol with an average of 6.5 ethoxyl units, polyhydroxy fatty acid amides, such as $C_{12}$-$C_{13}$ amide with N-linked methyl or N-linked reduced sugar. Anionic surfactants can be included in any desired amount. In one embodiment, anionic surfactants are present in the amounts given above for surfactants.

Examples of zwitterionic/amphoteric surfactants include, but are not limited to, derivatives of aliphatic secondary and tertiary amines in which the aliphatic radical can be straight chain or branched and wherein one of the aliphatic substituents contains about 8 to about 18 carbon atoms and one contains an anionic water solubilizing group, e.g., carboxy, sulfonate, sulfate, phosphate, or phosphonate. Examples of such compounds include sodium 3-dodecyaminopropionate, sodium 3-dodecylaminopropane sulfonate, N-alkyl taurines and N-higher alkyl aspartic acids. Other equivalent amphoteric surfactants may be used. Examples of amphoteric surfactants include, but are not limited to, a range of betaines including, for example, high alkyl betaines, such as coco dimethyl carboxymethyl betaine, lauryl dimethyl carboxymethyl betaine, lauryl dimethyl alpha-carboxyethyl betaine, cetyl dimethyl carboxymethyl betaine, lauryl bis-(2-hydroxyethyl)carboxy methyl betaine, stearyl bis-(2-hydroxypropyl)carboxymethyl betaine, oleyl dimethyl gamma-carboxypropyl betaine, and lauryl bis-(2-hydroxypropyl)alpha-carboxyethyl betaine, sulfobetaines such as coco dimethyl sulfopropyl betaine, stearyl dimethyl sulfopropyl betaine, amido betaines, amidosulfobetaines and the like. Betaines having a long chain alkyl group, particularly coco, may be particularly useful as are those that include an amido groups such as the cocamidopropyl and cocoamidoethyl betaines. In one embodiment, the zwitterionic surfactant comprises cocamidopropyl betaine. Zwitterionic/amphoteric surfactants can be included in any desired amount. In one embodiment, zwitterionic/amphoteric surfactants are present in the amounts given above for surfactants.

Examples of nonionic surfactants include, but are not limited to, ethoxylated fatty alcohols (such as the steareth-2 to steareth-100 series from Croda Chemicals, Inc. sold under the trademark Brij, such as steareth-2, steareth-4, steareth-10, steareth-20, or steareth-100), polysorbate 20, long chain alkyl glucosides having $C_8$-$C_{22}$ alkyl groups; coconut fatty acid monoethanolamides such as cocamide MEA; coconut fatty acid diethanolamides, fatty alcohol ethoxylates (alkylpolyethylene glycols); alkylphenol polyethylene glycols; alkyl mercaptan polyethylene glycols; fatty amine ethoxylates (alkylaminopolyethylene glycols); fatty acid ethoxylates (acylpolyethylene glycols): polypropylene glycol ethoxylates (for example the Pluronic™ block copolymers commercially available from BASF); fatty acid alkylolamides, (fatty acid amide polyethylene glycols); N-alkyl-, N-alkoxypolyhydroxy fatty acid amides: sucrose esters; sorbitol esters; polyglycol ethers; and combinations thereof. Nonionic surfactants can be included in any desired amount. In one embodiment, nonionic surfactants are present in the amounts given above for surfactants, for example from 1 to 25 weight %, preferably from 1 to 15 weight %.

The cleansing bars can contain water. In certain embodiments, the amount of water is greater than 0 (e.g., from 0.001%) to 20 weight %; to 15 weight %, to 10 weight %, from 5 to 20 weight %, or 5 to 15 weight %, or 10 to 20 weight %, or 10 to 15 weight %.

Optionally, the cleansing bar can contain foam boosters. Examples of foam boosters include, but are not limited to, certain amphoteric surfactants, cocomonoethanolamide (CMEA), cocoamidopropylamine oxide, cetyl dimethylamine chloride, decylamine oxide, lauryl/myristyl amidopropryl amine oxide, lauramine oxide, alkyldimethyl amine n-oxide, and myristamine oxide. in certain embodiments, the amount of foam booster is 2 to 10 weight %.

Optionally, the cleansing bar can contain any additional materials that are added to personal cleansing or laundry bars. Examples include, but are not limited to, skin conditioning agents, moisturizing agents, binders, foam boosters, coloring agents, fragrance, dyes and pigments, titanium dioxide, chelating agents such as EDTA, sunscreen active ingredients such as butyl methoxy benzoylmethane; antiaging compounds such as alpha hydroxy acids, beta hydroxy acids; preservatives such as hydantoins, imidazolines; humectants, polyols such as glycerol, sorbitol, propylene glycol and polyethylene glycols; particulate matter such as silica, talc, or calcium carbonate; antioxidants such as butylated hydroxytoluene (BHT); vitamins such as A, E, K and C; essential oils and extracts thereof such as rosewood and jojoba, particulate matter such as polyethylene beads, jojoba beads, lufa, or oat flour, fillers, exfoliating/scrubbing particles, pearlizers, inorganic salts, brighteners, sequestering agents, opacifiers, and mixtures of any of the foregoing components.

In one embodiment the cleansing bar includes fragrance in an amount of 0.001% to 2% by weight of the composition.

In one embodiment the cleansing bar includes pearlizers, such as titanium dioxide, in an amount of 0.01% to 1% by weight of the composition.

In one embodiment the cleansing bar includes one or more pigments, such as chromium oxide green, in an amount of 0.001% to 1% by weight of the composition.

In one embodiment, the cleansing bar includes silica, or silicon dioxide, incorporated at a level of from about 0.1% to about 15%, preferable from about 1% to about 10%, more preferably from about 3% to about 7%. Silica is available in a variety of forms, including but not limited to, crystalline, amorphous, fumed, precipitated, gel, and colloidal forms.

In one embodiment, the cleansing bar includes free fatty acids to provide enhanced skin feel benefits, such as softer or smoother feeling skin. Suitable free fatty acids include those derived from tallow, coconut oil, palm oil and palm kernel oil.

In a second exemplary embodiment, the invention includes a method (Method 1) of method of removing bacteria from skin comprising washing the skin with a cleansing composition according to any Composition 1 et seq.

In a third exemplary embodiment, the invention includes a method (Method 2) of method of inhibiting bacterial growth on skin comprising washing the skin with a cleansing composition according to any Composition 1 et seq.

Piroctone olamine is a solid at standard temperature and pressure (STP), and is typically sold as a powder. The inclusion of PO into a bar soap formula is challenging for at least the reasons that PO is relatively expensive; the addition of PO as a powder represents a process challenge; and when PO is added as a powder, the foam properties of the formula are significantly impacted.

In some embodiments, the invention includes a method (Method 3) of preparing a bar soap cleansing composition, the bar soap cleansing composition comprising at least one cleanser chosen from soaps and surfactants; and an antibacterial system; wherein the antibacterial system comprises an effective amount of a combination of phenoxyethanol and piroctone, or a salt thereof; the method comprising the steps of:
  providing a pre-mixture or pre-solution comprising piroctone, or a salt thereof, in a solvent; and
  incorporating the pre-mixture or pre-solution into a bar soap formulation; for example,
3.1 Method 3, wherein the solvent comprises phenoxyethanol, or propylene glycol, or a mixture of phenoxyethanol and propylene glycol.
3.2 Method 3, wherein:
  the solvent comprises propylene glycol;
  phenoxyethanol is present in an amount of from 0.01% to 2% by weight of the cleansing composition; and
  the piroctone, or salt thereof, is present in an amount of from 0.01% to 1.5% by weight of the cleansing composition;
3.3 Any preceding Method 3 et seq., wherein the cleansing composition further comprises petrolatum in an amount of from 0.1-0.9% by weight of the cleansing composition;
3.4 Any of Methods 3.1-3.3, wherein:
  the solvent comprises the phenoxyethanol or propylene glycol; and
  the pre-solution or pre-mixture comprising solvent and piroctone, or salt thereof, is prepared by combining solvent and piroctone or salt thereof, and optionally heating to a temperature up to 120° C.;
3.5 Method 3.4 wherein the solvent and piroctone or salt thereof, are heated to a temperature from 60-100° C.; or from 65-80° C.;
3.6 Any preceding Method 3 et seq., wherein the piroctone, or a salt thereof comprises piroctone olamine;

3.7 Any of Methods 3.1-3.5, wherein:
the piroctone, or a salt thereof comprises piroctone olamine;
the solvent comprises the phenoxyethanol or propylene glycol; and
the pre-mixture or pre-solution comprising solvent and piroctone, or a salt thereof, comprises from 1-30% by weight piroctone olamine in said pre-mixture or pre-solution;

3.8 Any of Methods 3.1-3.7, further comprising providing a second pre-mixture or pre-solution comprising piroctone, or a salt thereof, in a second solvent; and incorporating the second pre-mixture or pre-solution into the bar soap formulation;

3.9 Method 3.8 wherein the second solvent is selected from a fragrance, a fragrance dissolved in a solvent, propylene glycol, phenoxyethanol, ethanol, isopropanol, PEG 400, and glycerol.

3.10 Method 3, wherein the solvent is, or includes, propylene glycol;

3.11 Method 3.10, wherein:
phenoxyethanol is present in an amount of from 0.01% to 2% by weight of the cleansing composition; and
the piroctone, or salt thereof, is present in an amount of from 0.01% to 1.5% by weight of the cleansing composition;

3.12 Method 3.10 or 3.11, wherein the cleansing composition further comprises petrolatum in an amount of from 0.1-0.9% by weight of the cleansing composition;

3.13 Any of Methods 3.10-3.12, wherein the pre-solution or pre-mixture comprising piroctone, or salt thereof, and propylene glycol is heated to a temperature from 40-80° C.; or from 50-70° C.; or about 60° C.;

3.14 Any of Methods 3.10-3.13, wherein the piroctone, or a salt thereof comprises piroctone olamine;

3.15 Any of Methods 3.10-3.14, wherein the pre-mixture or pre-solution comprising propylene glycol and piroctone olamine, or a salt thereof, comprises from 1-16% by weight piroctone olamine in said pre-mixture or pre-solution;

3.16 Any of Methods 3.10-3.15, further comprising providing a second pre-mixture or pre-solution comprising piroctone, or a salt thereof, in a second solvent; and incorporating the second pre-mixture or pre-solution into the bar soap formulation;

3.17 Method 3.16, wherein the second solvent is selected from a fragrance; a fragrance dissolved in a solvent, propylene glycol, phenoxyethanol, ethanol, isopropanol, PEG 400, glycerol and mixtures thereof;

3.18 Any preceding Methods 3 et seq., wherein the at least one cleanser component comprises from about 30, 40, 50 or 60% by weight of the composition to about 70, 80, 85, 90 or 95% by weight of the composition.

3.19 Any preceding Methods 3 et seq., wherein the piroctone, or a salt thereof and the solvent are pre-mixed together, e.g., wherein the piroctone, or a salt thereof is in powder form and combined with the solvent prior to being combined with any aqueous or hydrophilic soap components.

3.20 Any preceding Methods 3 et seq., wherein the heated pre-mixture is then blended with soap chips, and any other optional components of the final cleansing bar composition.

3.21 Any preceding Methods 3 et seq., further comprising the step of adding additional optional ingredients to the blended pre-mixture and soap mixture.

3.22 Any preceding Methods 3 et seq., further comprising the processing of the final composition to produce cleansing bars.

3.23 Any preceding Methods 3 et seq., wherein the product cleansing bars consist essentially of any one of Compositions 1 et seq.

3.24 A cleansing bar that is prepared according to any preceding Methods 3 et seq.

The present disclosure further provides the use of an antibacterial system comprising phenoxyethanol and piroctone olamine in the preparation of a cleansing formulation as described herein, for example wherein the cleansing formulation is a bar soap. The present disclosure further provides cleansing compositions prepared by the methods described herein.

In some embodiments, the piroctone, or salt thereof, is added to the soap formulation mixture in a pre-mixture or pre-solution. For example, piroctone olamine, which is a solid at standard temperature and pressure (STP), is conveniently dissolved in a suitable solvent, and optionally heated to form a pre-mixture, or where the heating effects dissolution of the piroctone olamine, a pre-solution. The resulting pre-mixture or pre-solution can then be combined with soaps, etc., in accordance with any suitable manufacturing protocol for producing cleansing bars as is known in the art.

In some embodiments, piroctone olamine is dissolved in a suitable amount of phenoxyethanol; i.e., all or part of the phenoxyethanol of the composition can be employed as the solvent for the piroctone olamine. Typically, where phenoxyethanol is the solvent for the piroctone olamine pre-mix or pre-solution, the piroctone olamine is present in the pre-mixture or pre-solution in an amount of from 1-30% by weight; for example 5%, 10%, 15%, 20%, 25% or 30% by weight. In such embodiments, the mixture including the piroctone olamine and phenoxyethanol is preferably heated to a temperature of from 50-120° C.; for example from 60-100° C.; for example from 65-80° C.; preferably to effect partial or complete dissolution of the piroctone olamine.

In some further embodiments, the solvent for the piroctone olamine in the pre-mix or pre-solution includes or consists of propylene glycol. Typically, where propylene glycol is the solvent for the piroctone olamine pre-mix or pre-solution, the piroctone olamine is present in the pre-mixture or pre-solution in an amount of from 1-16% by weight; for example 5%, 10%, 15%, or 16% by weight. In such embodiments, the mixture including the piroctone olamine and propylene glycol is preferably heated to a temperature of from 40-80° C.; for example from 50-70° C.; for example about 60° C.; preferably to effect partial or complete dissolution of the piroctone olamine.

In some embodiments, amounts of piroctone, or a salt thereof as described above can be supplemented by addition of a second pre-mixture or pre-solution comprising piroctone, or a salt thereof, in a second solvent, into the bar soap formulation. In some such embodiments, the second solvent can be a fragrance; or a fragrance dissolved in a solvent as described above. In addition to propylene glycol, phenoxyethanol and fragrance as described above, other solvents suitable for delivery of piroctone, or a salt thereof include surfactants, and solvents containing alcohol functional groups, such as for example ethanol, isopropanol, PEG 400, and glycerol.

The cleansing bars of the present disclosure may be prepared by any of the techniques known to those skilled in the art, including both batch processes and continuous processes. The first step in the preparation of the cleansing bar is typically the preparation of the soap component.

Techniques known to those skilled in the art may be used, such as the classic kettle boiling process or the modern continuous soap manufacturing process. For example, an appropriate fat, oil, or carboxylic acid, or mixture thereof, is first combined with a base (e.g., sodium or potassium hydroxide or carbonate) in the presence of water to form the soap component. The soap component can then be processed and purified to remove excess base and/or glycerol as needed, and formed into chips, pellets, noodles or other solid or semi-solid forms. Optional ingredients such as additional surfactants may also be added after the removal of excess base but before formation into chips, pellets or noodles. The soap component may then be ground up, suspended in water and combined with the piroctone, or a salt thereof, and phenoxyethanol; for example by use of a pre-mix or pre-solution as described above.

After addition of the pre-mixture or pre-solution, the mixture is processed together with the soap chips and any other desired ingredients, for example by stirring and/or grinding and/or blending, with heating if necessary. After processing, the final composition is then formed into the finished cleansing bar product.

The cleansing bar may be formed by the extrusion method, and may be of varying sizes and shapes such as ovoid or rectangular in shape with either a flat or curved profile as an overall appearance.

In some embodiments, the cleansing bars of the present disclosure can include petrolatum. It has been surprisingly discovered in accordance with the present disclosure that the inclusion of petrolatum is effective to improve the antibacterial efficacy of the piroctone-phenoxyethanol antibacterial system. Thus, in some embodiments, the cleansing compositions of the disclosure include petrolatum, preferably in an amount of from 0.1-05% by weight, from 0.1-2% by weight, or from 0.1-1% by weight, or from 0.3-0.9% by weight, from 0.3-0.7% by weight, or from 0.3-0.5% by weight of the cleansing composition; for example in an amount of 0.1%, 0.1%, 0.3%, 0.4%, 0.5%, 0.6%, 0.7% or 0.8% by weight of the composition. In some embodiments, the weight ratio of petrolatum to piroctone olamine present in the cleanser composition is from 10:1 to 1:2; for example from 5:1 to 1:2; for example from 4:1 to 1:2; for example from 3:1 to 1:1; for example 3:1. 2:1 or 1:1.

Exemplary embodiments of the present disclosure will be illustrated by reference to the following examples, which are included to exemplify, but not to limit, the scope of the present invention.

EXAMPLES

Example 1

Table 1 describes an exemplary composition of the present invention.

TABLE 1

| Ingredient | Wt % |
| --- | --- |
| Cleanser base | 85-98 |
| Phenoxyethanol | 0.1-2 |
| Piroctone Olamine | 0.01-1.5 |
| Petrolatum | 0.1-5% |
| Dye/Fragrance/Other ingredients | 0.02-5 |

Example 2

Performance properties (use up rate; slough test and cracking) are studied for soap bars containing either triclocarban (TCC) [Comparative Example I] or 0.75% phenoxyethanol (PE) and 0.3% piroctone olamine (PO) [Composition I].

Use up (or wear) rates for soap bars is determined by a procedure involving weighing the bars before and after multiple cycles that included hand washing employing the bars, and rinsing the bars, followed by drying the bars. A minimum of 2 bars are used, and the results are recorded as the average of the percent weight loss after a defined number of cycles.

The slough test determines the bar soap slough (i.e., the soft, mushy soap formed when a bar of soap sits in a puddle of water after a prolonged period of time) at high humidity and room temperature. The bars are pre-washed, and arranged in a water bath such that they are sitting in a puddle of water at 95° F. After a defined time, the bars are taken out; the slough removed; and the bars are dried. Results are reported as the average of % weight loss; i.e., the average of [(initial bar weight−final bar weight)/(initial bar weight)] for all the bars tested.

Cracking is determined by exposing the bars to water and drying them at room temperature, and visually inspecting them for cracks, and rating them on a scale of 0 to 5, where 0 is no cracking and 4-5 indicates severe cracking.

The results of these evaluations are described in Table 2 (below).

TABLE 2

| Property | Comparative Example I | Composition I |
| --- | --- | --- |
| Use up rate | 8.1% | 7.5% |
| Slough Test | 11.5% | 10.8% |
| Cracking | 0 | 0 |

It can be seen that the exemplary composition of the present invention (Composition I), comprising 0.75% PE and 0.3% PO, has superior use up rate and slough test results relative to the comparative example which contains TCC.

Example 3

The antibacterial efficacy of cleansing compositions containing 0.75% PE+various % of PO (0.1%, 0.2% and 0.3%) is evaluated by testing the residual antibacterial (AB) performance in an in vitro system where the PE and PO are delivered from the bar soap to pig skin.

Ex-vivo Porcine skin is washed with the soap bars using a procedure that simulates a consumer hand wash to evaluate residual antibacterial efficacy. Using a gloved hand, porcine skin and bar soaps are moistened under running tap water (6 L/min). The bar soap is rubbed against the substrate for 15 seconds using light pressure. The substrate is then lathered for 45 seconds. The substrate is then rinsed for 15 seconds by holding the substrate at a 45 degree angle and allowing the water to impinge on the top of the substrate and cascade across the entire surface. Substrate is then lightly patted dry and allowed to air dry for 15 minutes before bacteria inoculation. Following appropriate drying time a circular area is delineated on the substrate and the center of the circular area inoculated with 0.025 ml of bacteria inoculum. Substrate is then incubated for appropriate time at 33° C. At the desired/appropriate time point the bacteria is harvested using a glass cylinder cup, area=7.1 cm$^2$ using Letheen Broth. Harvesting involves pipetting 2 mL of Letheen Broth into a hollow glass cylinder and then massaging the skin for 60 seconds with a sterile glass rod and transferring the fluid to a test tube. The samples are then serially diluted 10-fold in Letheen Broth and plated on Microbial Content Agar (MCA), $10^3$-$10^4$ dilutions. The MCA plates are incubated at 33° C. for a minimum of 24 hours. A count for a colony forming unit (CFU) is given for measurements in the range of 30-300. If no counts are observed, those plates with the CFUs closest to the range are used. The mean $Log_{10}$ CFU/cm$^2$ is calculated, as is the Log reduction of the product calculated by subtracting the water control and/or placebo—the test sample (Log reduction=Log of Input of Control CFU−Log of Sample CFU). The results are shown in Table 3 (below).

TABLE 3

|  | 0.1% TCC | 0.75% PE + 0.1% PO | 0.75% PE + 0.2% PO | 0.75% PE + 0.3% PO |
|---|---|---|---|---|
| Mean Log (CFU/7.1 cm$^2$) Reduction vs Placebo (S. Aureus) | 1.83 | 0.21 | 0.96 | 1.78 |
| Mean Log (CFU/7.1 cm$^2$) Reduction vs Placebo (E. coli) | 2.81 | 1.00 | 0.87 | 1.40 |

The results described in Table 3 (above) show the residual antibacterial performance of the PE/PO antibacterial system delivered by the bar soaps. These results show that at a PE level of 0.75%, increasing PO level enhances the Log reduction of the formula.

Example 4

Experiments are conducted to examine the antibacterial efficacy of 0.75% phenoxyethanol/0.3% piroctone olamine plus petrolatum at various concentrations (0.3%-0.9%) delivered from a bar soap against E. coli, using the micro test described above. The results are shown in Table 4 (below).

TABLE 4

|  | 0.75% PE + 0.3% PO | 0.75% PE + 0.3% PO + 0.3% Petrolatum | 0.75% PE + 0.3% PO + 0.5% Petrolatum | 0.75% PE + 0.3% PO + 0.7% Petrolatum | 0.75% PE + 0.3% PO + 0.9% Petrolatum |
|---|---|---|---|---|---|
| Mean Log (CFU/ml) Reduction vs Initial Population | 1.44 | 2.64 | 2.70 | 1.79 | 1.12 |

The results described in Table 4 (above) show that the addition of petrolatum to the PE/PO mixture improved antibacterial performance by one log unit. These results also show that a range of petrolatum loading levels enhance the antibacterial performance of compositions comprising a combination of PE and PO.

Example 5

Experiments are conducted to quantify the deposition of piroctone olamine in an in vitro skin model. VITRO-SKIN® is removed from its protective packaging using gloves, and is cut into 5 cm×5 cm (2"×2") squares using a paper cutter. Each piece is placed on a shelf/tray inside a humidity chamber, taking care to not overlap the VITRO-SKIN® pieces. The pieces are then incubated in the closed, controlled-humidity chamber for 16 to 24 hours prior to product application/deposition studies.

A 2 liter beaker of deionized water is pre-heated to 40° C.±2° C. A thermometer is inserted to maintain/monitor at 40° C.±2° C. for the duration of the experiment. The running of tap water is started in a sink at 35° C.±2° C., using a faucet thermometer to maintain 35° C.±2° C. for the duration of the experiment. One 2"×2" piece of pre-hydrated vitro skin from the controlled-humidity chamber is dipped for 5-10 seconds, using tweezers, in the pre-heated 40° C. deionized water. The wet piece is placed (rough side of skin up) piece on a clean plastic surface, with 2-3 layers of paper towels underneath (transparency film, or acetate, as commonly is used with overhead projectors was typically used as the plastic surface). A new clean plastic surface/acetate is used for subsequent skin sample(s).

Test bar #1 is rotated in a gloved hand (using only disposable poly gloves from VWR International) 10 times under the 35° C.±2° C. tap water. Once finished rotating, Test bar #1 is allowed to stand to drain off any residual water into the sink.

Working on the plastic surface, the wetted soap bar is taken and applied to the skin sample for 15 seconds (using a timer) with minimal force, being careful not to rip the skin in the process. Care is taken to try and rotate bar quickly to use all sides of soap during this process.

The bar is placed aside, and the treated skin surface is lathered (massaged) with an index finger, using minimal (not excessive) force, for 45 seconds, using a timer. Using tweezers, the treated skin is quickly taken to a deionized RT water machine and rinsed under the running nozzle stream for 15 seconds, using a timer. Using tweezers, the rinsed vitro skin is placed on paper towels until completely dry (usually 3-4 hours).

The steps above are repeated with subsequent soap bars. When completely dry, the skin(s) are ready for HPLC analysis, and the Extraction Procedure.

The pieces of VITRO-SKIN® are carefully cut into approximately 9-16 small pieces using tweezers/forceps to hold the pieces during cutting. The cuttings are collected on filter paper, and then poured into labeled scintillation vials. These steps are repeated for all replicates/test samples. 5 ml of ethanol is added to each sample, and the vials are well vortexed. The sample lids are closed, and the samples are allowed to sit for 24 to 48 hours to extract the PE from the VITRO-SKIN® (shorter exposure times can lead to high variability in the results). The times of the extractions are recorded. The ethanol is removed from the vials using disposable glass Pasteur pipettes, and as much of the ethanol extraction as possible is transferred into a labeled Kimble Tube. The ethanol is evaporated from the Kimble tubes with an evaporator (such as GENEVAC). Alternatively, the ethanol can be evaporated over time with open caps. The samples are capped and stored in the refrigerator until reconstitution with controlled volumes of solvent and subsequent HPLC analysis. The results are shown in Table 5 (below).

TABLE 5

|  | Control (0.3% PO) | 0.3% PO + 0.75% PE | 0.3% PO + 0.75% PE + 0.75% Petrolatum |
|---|---|---|---|
| ppm of PO Deposited | Appx. 7.0 | Appx. 7.2 | Appx. 9.0 |

Example 6

Experiments are conducted to determine the antibacterial efficacy of 0.75% phenoxyethanol delivered from a bar soap, with and without use of PE as solvent during processing, using the procedure of Example 2 (above). The results of the three (3) hour Ex-vivo Porcine Skin in vitro Cup-Scrub studies vs *E. coli* are shown in Table 6 (below).

TABLE 6

|  | 0.75% PE | 0.3% PO | 0.75 PE + 0.3% PO | 0.3% PO dissolved in 0.75% PE + 0.75% Petrolatum |
|---|---|---|---|---|
| Mean Log (CFU/7.1 cm$^2$) Reduction vs Placebo (*E. coli*) | 1.22 | 0.44 | 0.46 | 2.23 |

The results described in Table 6 (above) demonstrate that that 0.75% phenoxyethanol and 0.3% piroctone olamine delivered individually from bar soap provide a 1.22 and 0.44 log reduction vs. non-antibacterial placebo bar soap, respectively. The data indicates that the addition of petrolatum (0.75%) to the combination of piroctone olamine and phenoxyethanol provides a significantly greater log reduction (2.23) then either phenoxyethanol, piroctone of amine or the combination of both.

The data above show the feasibility of adding piroctone olamine as a phenoxyethanol solution up to at least 30% w/w during bar soap manufacturing, if heated, for example to 80° C. Furthermore, some piroctone olamine can optionally be supplemented as a solution in a further solvent, such as a fragrance or a fragrance dissolved in a solvent, preferably up to 7.5% at room temperature.

The in vitro skin deposition study demonstrates significantly enhanced deposition versus control, and the micro testing suggests solubilizing piroctone olamine in phenoxyethanol provides an additional benefit for antibacterial activity.

Example 7

Experiments are conducted to determine the antibacterial efficacy of 0.75% phenoxyethanol delivered from a bar soap, with and without use of propylene glycol as a solvent during processing, using the procedure of Example 2 (above).

A PO/PG 15% pre-mix solution is prepared by mixing 15 g of piroctone olamine with 85 g of propylene glycol (PG) and heating to 60° C. for 10 minutes, at which time a colorless solution is formed. The premix is added to an amalgamator, and mixed with a cleanser base to obtain a batch of bar soap, with final levels of 0.75% PE and 0.3% PO. A similar batch is prepared except that the PO is added as a solid powder, and not dissolved in PG. Incorporation of the PO into the formula is significantly improved by use of the pre-mixture, as compared to addition of PO as a solid.

A three (3) hour Ex-vivo Porcine Skin in vitro Cup-Scrub study vs. *E. coli* is pre-formed on the bar soaps as described above in Example 3. The results are shown in Table 7 (below)

TABLE 7

|  | 0.75% PE + 0.3% PO (added as powder) | 0.75% PE + 0.3% PO (added dissolved in PG) |
|---|---|---|
| Mean Log (CFU/7.1 cm$^2$) Reduction vs Placebo (*E. coli*) | 0.46 | 1.47 |

The results show that the addition of PO as a pre-mixture in PG provides a significant increase in the Mean Log Reduction vs. Placebo, indicating an increased antibacterial efficacy compared to adding PO as a solid (powder).

Example 8

Experiments are conducted to determine the foaming properties of: (1) a bar soap containing 0.75% PE; (2) the same formula additionally containing 0.3% PO, wherein the PO is added as a powder; and (3) the same formula additionally containing 0.3% PO, wherein the PO is added in PG solvent as described in Example 6 (above).

The foaming properties of the bar soaps are determined in a proprietary system that measured several foaming parameters including amount of foam, foam density, foam stability and foam fluidity. The results of these evaluations demonstrate that the foaming properties of a bar soap containing 0.75% PE (1) and the formula containing 0.3% PO added in PG solvent (3) were at parity, while the formula containing 0.3% PO added as a powder (2) displayed inferior foaming properties.

These results confirm that the use of PG as a solvent for PO in bar soap formulations significantly improves incorporation of PO into the final formula, and also improves the manufacturing process. It also significantly increased the antibacterial efficacy of the formulation, which is beneficial in terms of potency and the potential for reducing the PO level, and therefore reducing the cost of PO in the formulation. It also helps mitigate the performance impairment (i.e., reduced foaming) that might be expected with the use of PO.

What is claimed is:

1. A personal care composition, comprising
   a cleanser base wherein, the cleanser base comprises at least one cleanser chosen from a soap and a surfactant; and
   an effective amount of an antibacterial system consisting of: phenoxyethanol, piroctone olamine, and petrolatum;
   wherein the phenoxyethanol is present in an amount of from 0.01% to 2% by weight of the personal care composition;
   wherein the piroctone olamine is present in an amount of from 0.01% to 1.5% by weight of the personal care composition; and
   wherein the petrolatum is present in an amount of from 0.1% to 0.9% by weight of the personal care composition.

2. The personal care composition of claim 1, wherein the composition further comprises propylene glycol.

3. The personal care composition of claim 2, wherein the composition is a cleansing bar.

4. The personal care composition of claim 1, wherein the phenoxyethanol is present in an amount of from 0.1% to 1.25% by weight; or from 0.5% to 1% by weight; or from 0.65% to 0.85% by weight; or about 0.75% by weight of the personal care composition.

5. The personal care composition of claim 1, wherein the piroctone olamine is present in an amount of from 0.01% to 1% by weight; of from 0.01% to 0.5% by weight; of from 0.05% to 0.3% by weight; of from 0.05% to 0.15% by weight; of from 0.2% to 0.4%; or about 0.1% by weight; or about 0.3% by weight of the personal care composition.

6. The personal care composition of claim 1, wherein the petrolatum is present in an amount of from 0.1% to 0.5% by weight; or from 0.3% to 0.9% by weight; or from 0.3% to 0.7% by weight; or from 0.3 to 0.5% by weight of the personal care composition.

7. The personal care composition of claim 1, wherein the phenoxyethanol is present in an amount of from 0.65% to 0.85% by weight of the personal care composition.

8. The personal care composition of claim 1, wherein the piroctone olamine is present in an amount of from 0.2% to 0.4% by weight of the personal care composition.

9. The personal care composition of claim 1, wherein
   the phenoxyethanol is present in an amount of from 0.65% to 0.85% by weight of the personal care composition;
   the piroctone olamine is present in an amount of from 0.2% to 0.4% by weight of the personal care composition; and
   the petrolatum is present in an amount of from 0.3% to 0.9% by weight of the personal care composition.

10. The personal care composition of claim 1, wherein the personal care composition comprises two or more surfactants or soaps.

11. The personal care composition of claim 1, wherein the at least one cleanser comprises soap chips, anionic surfactants, nonionic surfactants, cationic surfactants; amphoteric surfactants, and zwitterionic surfactants.

12. A method of removing bacteria from skin comprising washing said skin with a personal care composition according to claim 2.

13. A method of inhibiting bacterial growth on skin comprising washing said skin with a personal care composition according to claim 2.

* * * * *